United States Patent [19]
Thrall et al.

[11] Patent Number: 5,645,823
[45] Date of Patent: Jul. 8, 1997

[54] KERATINOUS TISSUE CONDITIONER

[76] Inventors: Bernice Eileen Thrall; Judith Ann Noel, both of P.O. Box 479, La Salle, Colo. 80645

[21] Appl. No.: 499,357

[22] Filed: Jul. 7, 1995

[51] Int. Cl.⁶ .................................................. A61K 7/04
[52] U.S. Cl. ............................................ 424/61; 424/400
[58] Field of Search ............................ 424/80, 70.16, 424/61, 70.17, 73, 443

[56] References Cited

U.S. PATENT DOCUMENTS

| | | | |
|---|---|---|---|
| 2,108,765 | 2/1938 | Domagk | 167/30 |
| 2,152,047 | 3/1939 | Hahl et al. | 167/33 |
| 4,286,609 | 9/1981 | Miller | 132/75 |
| 4,530,828 | 7/1985 | Smith et al. | 424/61 |
| 4,604,283 | 8/1986 | Gresham | 424/80 |
| 4,897,261 | 1/1990 | Yamazaki et al. | 424/61 |
| 4,996,043 | 2/1991 | Adamich-Saltman | 424/61 |
| 5,133,958 | 7/1992 | Stuckler | 424/61 |
| 5,143,721 | 9/1992 | Beachy | 424/61 |
| 5,147,651 | 9/1992 | Hobson et al. | 424/443 |
| 5,338,541 | 8/1994 | Matz et al. | 424/71 |
| 5,486,537 | 1/1996 | Farinas | 514/462 |

OTHER PUBLICATIONS

Helmut Sigel, editor, Metal Ions in Biological Systems, vol. 2, pp. 7–196, Marcel–Decker, Inc., NY, 1973.
Jeffrey, G.A. and W. Saenger, Hydrogen Bonding in Biological Structures, pp. 351–479, Springer–Verlag, NY, 1991.
Orfanos, C.E., et al., editors, Hair Research, Proc. Int. Congr., 1st, 1979 (Pub. 1981), pp.96–115 (Eng.).

*Primary Examiner*—Thurman K. Page
*Assistant Examiner*—William E. Benston, Jr.

[57] ABSTRACT

A composition that describes a clear, colorless, odorless, aqueous solution that is safe and effective in restoring and maintaining normalcy of the keratinous tissues and the adjacent tissues of finger and toe nails and equine hooves. Cracking, splitting, peeling and breakage of nails and hooves caused by environmental factors that denature peptide bonds of keratin, interrupts water and lipid balance and further interrupts growth and normal metabolic processes, is stopped and compositional balance is re-established by application of the solution. The composition is effective for keratinous tissues that are either too dry or too wet. Application by dropper bottles or sprays is quick, easy and not messy. Beneficial effects are observed in 1–2 weeks and reinforcement treatments are required only once or twice per week, or as required to maintain normal status.

20 Claims, No Drawings

KERATINOUS TISSUE CONDITIONER

FIELD OF INVENTION

The present invention relates to a safe aqueous solution used for restoring and maintaining the compositional balance of normal, healthy keratinous tissues and their adjacent structures, and more particularly for treatment of damaged finger and toe nails and equine hooves.

BACKGROUND OF THE INVENTION

Cracked, split, peeling and broken finger and toe nails and equine hooves are not only unsightly, but a nuisance that can be painful and even crippling. Such conditions provide entry opportunities for infections, and foreign bodies such as sand which can lead to deep abscesses in horses hooves.

The hard outer shells of nails and hooves are composed mainly of long, tubular strands of protein called keratin. The tubular strands are made up of long chains of amino acids called peptides, or polypeptides. Under normal conditions, the peptide chains are held tightly by linking together, or twining, with the aid of water and minerals which help form strong bonds. Damage to keratinous tissues and their adjacent structures often occurs in apparently normal, healthy individuals, as opposed to conditions of illness or nutritional deficiencies. Some factors that are known to damage such proteins are heat, acid or alkaline compounds and urea. Fortunately, if the damage is not too severe, the effects can be reversed.

Environmental factors such as over-exposure to dry, arid, low humidity areas cause the keratinous fibers to shrink, pull apart, and become hard and brittle. Conversely, over-exposure to extremely wet, humid areas cause keratinous fibers to swell excessively, leaving the structure to soft and friable to withstand normal usage. Both conditions expose surface keratins and deep inner tissues to bacteria and other elements that can cause additional damage.

The relative inactivity of confined horses that minimizes blood circulation and natural abrasion, compared to that of horses in their natural, wild environment, is a major contributing factor to problem hooves. In the case of more confined horses, exposure to highly alkaline or acidic soils, and constant contact with bacteria, fungi and molds, stalls and corrals that are too dry or wet with urine and manure are additional factors that can contribute to problem hooves.

Gelatin and other hydrolyzed proteins, amino acids, urea, tars, fats and oils, vitamins, clays, resins, nitrocellulose, cholesterol, esters, alcohols, polymer emulsions, and phenols are only a few of the compounds added to formulations for hooves and nails.

Soaps, detergents, acid and alkaline compounds, organic solvents, acrylics, vinyls, lacquers, bacteria, fungi, and a plethora of chemicals and elements, unknowingly in daily use in lotions, potions and polishes, as well as, in the atmosphere conceivably contribute to the loss of integrity of keratinous tissues.

Daily doses of vitamins A, E and biotin are frequently recommended or incorporated into formulations to improve nail or hoof conditions. U.S. Pat. No. 5,133,958 recommends taking daily oral doses of a multi-vitamin mixture, plus many other adjuvants, and especially containing specific amounts of trigonelline and vitamin B-6 for a minimum of 20 days to begin seeing benefits. The present invention gives obvious results in about one week, and does not assume vitamin deficiencies.

U.S. Pat. No. 5,143,721 recommends rubbing nails for one-half minute each, twice a day, with dolomite powder to reduce peeling and cracking after a few weeks. This method is tedious and time consuming, and does not address the underlying causes and effects of damage as does the present invention.

U.S. Pat. No. 4,286,609 uses a hot oil and water treatment for dry, brittle nails and cuticle that involves a bath for holding the hot mixture and a cuticle stick. The oil mixture contains animal and vegetable oils, emollients, vitamins, protein hydrolysates, an antioxidant and fragrance, in which the fingernails are soaked 3–5 minutes for a recommended 28 treatments. The present invention requires no equipment or tools, does not use an emulsion of oils, etc., is quick, clean and easy to use, and would not present the problem of disposing used oils.

U.S. Pat. No. 4,530,828 describes usage of an emulsion composed of soap, urea, hydrolyzed animal protein, oil, cholesterol, and other compounds to produce creams or lotions. Rubbing the cream or lotion into the nails is said to relieve dry, brittle nails for 4–6 hours. The present invention contains no ingredients that might cause further denaturation of proteins; contains no emulsion of oil and water that might be only slowly absorbed, but uses instead short chain fatty acids that are combined to water soluble compounds that are readily absorbed; improvements last for days to weeks; application is quick, easy and not messy.

U.S. Pat. No. 4,897,261 presents a cosmetic, nail polish, composition said to have a high safety factor against peeling of dry nail tips. While their complex formulation might be beneficial for persons using nail polishes by reason of personal preference. The present invention not only provides strong healthy nails for non-cosmetic users, it also provides a strong base for persons who do use nail polishes.

U.S. Pat. No. 5,147,651 addresses similar problems in horses hooves by using oil and water emulsions to which a medicinal compound is added, then all is mixed into a pine tar carrier that is added to a filler of polyolefin fibers to provide a packing for the bottom of hooves. This is definitely messy compared to the clear, clean, aqueous solution of the preset invention.

U.S. Pat. No. 4,996,043 presents a composition to correct dry hooves by applying an emulsion of triglycerides, from animal or vegetable oils, polysaccharides and water formulated into a cream that also contains emollients, antioxidants, antimicrobials, flyspray, silicone oil and other adjuvants. Emphasis was placed on the importance of an oleic:linoleic acid ester ratio equal to or greater than one. Polysaccharides were seen as the principle water incorporating compounds, and silicone oil was used to minimize dirt cling to the hoof wall. Daily application and buffing were required for three weeks followed by application 3 to 5 times per week to maintain healthy hooves. The present invention takes advantage of the anti-static properties of a non-ionic surfactant to minimize dirt cling and to aid in water incorporation into inner structures of the hoof. The antimicrobial agent used in the present invention is also an antifungicidal compound the kills and inhibits recurrence of thrush, one of the most common hoof infections. The ease of use, and long lasting residual activity minimizes the number of daily applications and subsequent maintenance applications required by the present invention.

Cuticle softeners or removers traditionally used strongly alkaline solutions which cause the cells to swell, making the tissue easier to remove by cutting or pushing back. Among the chemicals used were aqueous potassium hydroxide, trisodium phosphate, and triethanolamine. Understandably, these chemicals can be irritating to the skin around the nails.

The present invention is not irritating, being a dilute aqueous solution having a pH around neutral. It also contains a desquamating component that minimizes cuticle without cutting or pushing back, and it also contains a component to help maintain a softness to the cuticle.

The safety of products is of great concern to users of cosmetics and cosmetologists, as well as, horse owners, veterinarians, and those concerned with the environment and disposal of used chemicals, Hygiene is another area of concern. To minimize the insidious effects of bacteria and fungi is to promote the health of nails and hooves. The principle compound of the present invention addresses both the safety and hygienic problems directly and efficiently.

The antimicrobial agent used in the present invention was developed in 1993, U.S. Pat. No. 2,108,765 and in 1934, U.S. Pat. No. 2,152,047 as a preservative and disinfectant. The compound was found to be useful as a preservative for meats and vegetables, thus demonstrating its long lasting, residual effects as observed in our testing. It was projected at that time to possibly be useful as a disinfectant in cosmetics such as face powders, face waters, gargles and the like, and for hyperidrosis.

The antimicrobial agent used in the present invention was selected from the class of quaternary ammonium compounds because of its widespread usage and proven safety. It has been used world-wide in hospitals, clinics and veterinary services as a pre-surgical scrub to facilitate removal of dirt, bacteria and desquamating epithelium. It has been used for irrigation of eyes, ears, and other mucous membranes. Purification of water supplies, detergent disinfectants, and sanitizers, are only a few additional uses of this compound. It is a broad spectrum bacteriocide, fungicide and virucide that is effective in very dilute solution, e.g., 1:500 to 1:40,000, or 0.2% to 0.0025%, respectively. Individual sensitivity to the compound is rare. Thus, the safety for all concerned and the hygienic properties of the most active component of the formula are well established.

In addition to the disinfecting properties, it has been shown that quaternary ammonium compounds such as the one used in the present invention can combine with proteins and can catalyze cross linking of peptide chains which affects strong stability.

Loss of water and/or lipids from keratinous tissues, or their adjacent structures would result in inactivation of metabolic systems. Peptide chains would shrink in diameter, shorten and pull apart exposing inner structures to microorganisms and other environmental factors to further interrupt the normal activity of metabolism. Excessive moisture, which causes welling and softening of the fibers, similarly expose inner structures to environmental factors that interrupt normal functioning of systems. The metabolic activity of electrolysis, oxidation and reduction, energy production, nutrient transport, and water barriers would all be interrupted, and the compositional balance and functions of normal healthy tissues would not be attained.

Emulsions of long chain (C-14–C-18) animal and/or vegetable oils and water are slow to breakdown, and they are usually further stabilized with compounds to prevent breakdown, additionally delaying any possible absorption. The present invention uses shorter chain (C-9–C-16) fatty acids combined with cyclic components that are water soluble and easily absorbed together with water, thereby, being available to supply energy or enter into any of the other functions of lipids and cyclic compounds.

The present invention corrects many problems of the prior art by re-establishing compositional balance and normal functions of keratinous tissues and their adjacent structures. Application of the composition described herein is by dropper bottle or spraying a clear, clean, aqueous solution. The solution is rapidly absorbed (about 1 minute for nails and about 3 minutes for hooves). Noticeable improvement in nail and hoof condition can usually be seen in 7–10 days. Residual effects are long lasting and may require reinforcement only once or twice a week depending on changing environmental conditions and usage. Fungal and/or bacteriocidal invasions of both surface and deep tissues are stopped in one or two treatments and re-infections minimized by the residual effects of the principal component and establishment of healthy tissues.

SUMMARY OF THE INVENTION

The primary object of the present invention is to provide a solution for restoring and maintaining the compositional balance of normal healthy keratinous tissues and their adjacent structures.

Another object of the present invention is to provide an aqueous solution that is safe and effective for restoring and maintaining the healthy compositional balance of finger and toe nails and their adjacent tissues.

Another object of the present invention is to provide an aqueous solution that is safe and effective for restoring and maintaining the healthy compositional balance of equine hooves and their adjacent tissues.

Another object of the present invention is to provide a method of treatment that is quick, easy and not messy to apply to finger and toe nails and equine hooves and their respective adjacent structures.

Another object of the present invention is to provide a safe, non-irritating means of curing bacterial and fungal infections with good residual properties.

Another object of the present invention is to provide a safe aqueous solution that will rapidly penetrate keratinous tissues and their adjacent structures with the active ingredients necessary to restore and maintain normal, healthy functions that are peculiar to each tissue.

The principle active ingredient is a well known cationic surfactant that has time tested, antiseptic properties that cleans and disinfects both surface and deep tissues of nails and hooves. Other supporting and enhancing agents of the formulation are a chelating compound, a non-ionic surface active agent, a moisturizing compound and a buffer. The aqueous solution is applied by drops or by spraying nails and hooves. Absorption occurs in 1–3 minutes.

Nails and hooves quickly stop cracking, splitting, peeling and breaking as healing begins when keratinous tissues are cleansed and disinfected, brought into water balance, supplement with lipids, and metabolic systems are activated. Nails and hooves not only harden, but they become tough, such that resiliency returns and normal activity is no longer damaging. At the same time cuticle tissues of finger and toe nails is minimized and remains soft. Tissues of the coronet band, frog and heel bulbs of horses resume their normal expansion, contraction and shock absorbing functions.

Other objects of this invention will appear from the following description and appended claims.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENTS

The composition of this invention provides a clear, colorless, odorless, aqueous solution that assists in repairing environmentally damaged keratinous tissues and their adjacent structures, especially those of human finger and toe nails and equine hooves. By adjacent structures, we are referring to the cuticle, the surrounding skin, growth root, and matrix underlying the surface of finger and toe nails; as relates to equines, we are referring to the coronet band, sole, frog, heel bulbs, and the matrix beds underlying the respective surfaces.

The basic components that comprise this invention are within the following ranges:

| Component | Percent by weight |
| --- | --- |
| Water | 65–99 |
| Antimicrobial | 0.0–10.0 |
| Chelating agent | 0.1–15.0 |
| Alkylated nonionic surfactant | 0.0–5.0 |

It is understood that the percentages of the above components will total 100 percent by weight and if other ingredients are included in the formulation, the percentages of all ingredients will total 100 percent by weight.

Distilled water is preferred, however, good quality deionized water would be acceptable.

The antimicrobial agent was selected from the class of quaternary ammonium compounds because of its widespread usage and proven safety. This class of compounds, also known as cationic surfactants, meaning only compounds that have an overall positive charge that lowers surface tension, includes such compounds as: steryl trimethyl ammonium chloride, or lauryl trimethyl ammonium chloride, disteryl dimethyl ammonium chloride or dialkyl dimethyl ammonium chloride, alkyl isoquinolinium salt, alkyl dimethyl benzylammonium chloride, and alkyl ethylbenzyl ammonium chloride, or cetyl pyridinium chloride, or the like. The most preferred agent being a mixture of n-Alkyl dimethyl benzyl ammonium chloride and n-Alkyl dimethyl ethylbenzyl ammonium chloride such as that developed by Stephan Co., Trademark BTC 2125M, also known as benzalkonium chloride. The alkyl groups consist generally of 29% lauric acid (C-12), 37% myristic (C-14), 7% palmitic (C-16), and 2% stearic (C-18).

Benzalkonium chloride was found to have at least 5 important functions. Reducing surface tension permits rapid absorption into both surface and deep tissues, where the disinfecting properties are active, and where catalysis of cross linking between peptide chains occurs.

A chelating agent such as ethylenediaminetetraacetic acid, commonly known as EDTA, or its salts, preferably mono sodium, was incorporated as a metal chelator to catalyze metal and hydrogen bonding to peptides.

A nonionic surfactant, that also lowers surface tension, was incorporated to facilitate penetration of water and other compounds through organic surfaces and to provide antistatic properties, especially to hoof walls. Representative of such compounds are: polyoxyethylene sorbitan monooleate, polyoxyethylene sorbitan monostearate or polyoxyethylene glycerol, monooleate polyoxyethylene glycerol, or nonyl phenoxypolyoxyethylene ethanols, octylphenoxy polyethoxyethanol, or with other alkyl substitutes; another group of nonionic surfactants with similar properties are such as: polyalkylene oxide-modified polydimethyl siloxanes, e.g., "Silwet" Trademark by OSi Specialties, Inc. The preferred nonionic surfactant used for this formulation was a mixture of hydrophillic ethylene oxide and hydrophobic nonyl phenol, or alkylphenoxypolyoxyethylene ethanols, such as that produced by Stephan Co., Trademark MAKON series, where the alkyl groups are C-9–C-10.

In addition to the basic four components it was found necessary to include a hygroscopic agent which was selected from a group of sugar alcohols, such as: glycerol, hexitol, penitol or sorbitol, or sodium lactate, sodium pyrroloidone carboxylate, or glycerol ethylene oxide. The additional moisturizing agent, preferably glycerol, was found to maintain softness of the nail cuticle and coronet band of hooves, and was incorporate within the range of 0.1–2.0% by weight of the total composition.

A buffering agent such as sodium citrate, or various acetate salts, and preferably citric acid, a known chelating agent was added within a range of 0.1–3.0% by weight of the total solution, or sufficient to bring the pH within a physiological range of 6.5–7.5, and to expand and enhance mineral translocation.

As all components of the formulation are compatible and highly water soluble, no special mixing instructions, other than thorough mixing, are required.

Application from high density polyethylene drip bottles or spray bottles in amounts sufficient to wet all surfaces of nails and hooves is simple, quick and clean. The solution may be spread by hand on the outer hoof wall to assure complete coverage. The hoof should be cleaned of excessive dirt and manure before usage.

A more preferred embodiment of the invention comprises:

| Component | Percent by weight |
| --- | --- |
| Water | 75–99 |
| Antimicrobial | 0.0–8.0 |
| Chelating agent | 0.5–10.0 |
| Alkylated nonionic surfactant | 0.0–3.0 |

Where the water is preferably distilled or deionized; the antimicrobial component was selected from quaternary ammonium compounds named above; the sequestering agent was similarly selected from the salts of ethylenediaminetetraacetic acids: and the nonionic surfactant selected from the compounds named above. The above named moisturizing agent was incorporated within the range of 0.1 to 1.5 percent by weight, and the buffering agent as named above was present within the range of 0.1 to 2.5 percent by weight.

A more highly preferred embodiment of the invention comprises:

| Component | Percent by weight |
| --- | --- |
| Water | 80–99 |
| Antimicrobial | 0.0–5.0 |
| Chelating agent | 0.1–5.0 |
| Alkylated nonionic surfactant | 0.0–2.5 |

Distilled or good quality deionized water are preferred. The antimicrobial was selected from the group of cationic surfactants or named quaternary ammonium compounds listed above. The sequestering agent was also as named above, and the nonionic surfactant similarly as named above. The moisturizing agent was added within the range of 0.1 to 1.0 percent by weight, and the buffering agent modified to within the range of 0.1 to 2.0 percent by weight.

It is understood that the percentages of all components will total 100 percent by weight.

The most preferred embodiment of the invention comprises:

| Component | Percent by weight |
| --- | --- |
| Water | 90–99 |
| Antimicrobial | 0.0–2.5 |
| EDTA | 0.5–2.5 |
| Alkylated nonionic surfactant | 0.0–2.0 |

Distilled or good quality deionized water is acceptable.

The antimicrobial agent was selected from the quaternary ammonium compounds such as those mention previously, and most preferably a mixture of n-Alkyl dimethyl benzyl ammonium chloride and n-Alykl dimethyl ethylbenzyl ammonium chloride, wherein the alkyl groups are from C-12 to C-18 (Stephan Co.).

The preferred sequestering agent being mono sodium ethylenediaminetetraacetic acid.

The nonionic surfactant was selected from the class of compounds such as those mentioned previously, with the most preferred being alkylphenoxypolyoxyethelene ethanol, where the alkyl groups are predominantly C-9 and C-10.

The moisturizing agent was selected from the class of sugar alcohols mentioned previously, with glycerol being the preferred hygroscopic agent used within a range of about 0.1 to 1.0 percent by weight.

The most preferred buffering agent, as described previously, was citric acid within a range of about 0.1 to 2.0 percent by weight, or an amount sufficient to adjust the pH to a physiological value of between 6.5 and 7.5.

EXAMPLE 1

A composition comprising the four basic components was tested on persons and horses with nail and hoof problems ranging from too dry and brittle to too soft, with undo splitting and breakage of both nails and hooves. The solution was effective in toughening nails in about one week and horse hooves in about 10 days, however, a common complaint of humans was that the cuticle was too dry. While the horses did not complain, it was noted that the coronet band appeared dryer than normal.

EXAMPLE 2

The prior formulation was modified to include glycerol within a range of 0.1–2.0%, and buffered with citric acid within a range of 0.1–2.0% sufficient to adjust the pH within a range of 6.5–7.5. The test was repeated and showed similar results for nails and hooves, with noticeably improved cuticle softness and softer, more normal coronet bands of horses.

EXAMPLE 3

Gelatin has long been recommended as a cure for damaged fingernails and incorporated into many formulas for both humans and horses. On this basis, the formula as described in Example 2 was modified to include 0.1–1.0% gelatin and again tested on human nails and equine hooves. The efficacy in nails appeared to be delayed to 2½–3 weeks, and about 4 weeks for horses. Consequently, this formula was abandoned.

Considering that benzalkonium chloride can combine with proteins to form derivatives, probably explains the delayed response to the formulation of Example 3.

Penetration of the keratinous tissues was observed by the rapid absorption of the solution, less than one minute for finger and toe nails, and less than three minutes for hooves. Penetration of the solution was also observed by the dissolution of clotted blood in inner layers of tissue as occurs when nails are bruised by hammers, etc., and as occurs in "stone bruises" seen within the sole tissue of hooves.

The efficacy of the solution for the treatment of thrust in horses can be observed after one or two days, and recurrence delayed by the residual effect of the antimicrobial agent and the restoration of healthy hooves.

Further evidence of the efficacy and residual effect of the solution was noted when treated finger and toe nails softened during bathing then became hard and tough again after drying.

Minerals reported in fingernails include: N, Ca, Zn, Cu, Fe, Na, F, Au, Hg, Mn, and Sb. The ash content of horses hooves was reported as 1.5%. Minerals are recognized as catalysts for chemical reactions, to maintain homeostasis of tissues, and to form very strong bonds with amino acids and peptides. Mixed-ligand complexes of more than one mineral element can form bonds with peptides, and some metals can eliminate or replace some of the hydrogen bonds. EDTA is a known carrier of metal ions and a known catalyst of bonding reactions. Critric acid is also a known metal chelating agent.

While mineral bonding to the peptides, or polypeptides, of keratin would impart a hardness and strength to the tubular fibers, hydrogen bonding to local side chain amino acids or peptides, and internal water impart flexibility. Cross linking would impart strength and tightening of the fibers which would express excessive water as seen in keratinous tissues that are too soft. Thus, explaining the efficacy of the solution for both nails and hooves that are too dry and brittle or too wet and soft.

Establishing a compositional balance and stimulating metabolic activity is necessary to affect the efficacy of the formulation. Providing lipids and other components of the compounds used in the formulation could conceivably enter into the metabolic processes, supplying energy, or for synthesis of compounds, or to become integral parts of the tissues.

The low concentrations and well known properties of all ingredients of the formulation essentially ensure the safety factor. Disposal of the solution presents no problem. No hypersensitivity was noted in either humans or horses tested.

The composition described in Example 2 appears to solve the fragile nail and hoof problems by helping fulfill the needs of the tissues; that is, by cleansing and disinfecting the tissues, strengthening the peptide bonds of keratin, supplementing lipids, and attaining normal water balance, thus, allowing resumption of normal metabolic and functional activities of nails and hooves.

Although the present invention have been described with reference to preferred embodiments, numerous modifications and variations can be made and still the result will come within scope or the invention. No limitation with respect to the specific embodiments disclosed herein is intended or should be inferred.

We claim:

1. A composition for the treatment and conditioning of keratinous, hairless, tissues and their adjacent tissues such as those of equine hooves and human finger and toe nails that have been damaged by environmental factors, consisting essentially of:

a. 65 to 99 percent by weight of water, and b. 0.0 to 10.0 percent by weight of an antimicrobial, and c. 0.1 to 15.0 percent by weight of a chelating agent, and d. 0.0 to 5.0 percent by weight of an alkylated nonionic surfactant;

e. said composition being a safe, aqueous solution of components that work in concert to supply water, liquids, and other organic compounds that rapidly penetrate a plurality of keratinous, hairless, tissues and a plurality of their adjacent tissues, to impart strength, hardness and flexibility necessary for normal functioning of said tissues;

f. said composition when applied to said keratinous, hairless, tissues and their said adjacent tissues restores and establishes normal, healthy metabolic function and compositional balance.

2. A composition for treatment and conditioning of said keratinous tissues and said adjacent tissues, according to claim 1, wherein:

a. said antimicrobial being an alkylated quaternary ammonium compound, and b. said antimicrobial being a cationic surfactant, and c. said antimicrobial being a broad spectrum bacteriocide and fungicide, and d. said antimicrobial having the property to catalyze cross-linking of peptide bonds.

3. A composition for treatment and conditioning of keratinous tissues and said adjacent tissues, according to claim 1, wherein:

a. said chelating agent being a salt of EDTA, and b. said chelating agent having the property to catalyze the formation of mixed-ligand complexes of metals and peptides.

4. A composition for treatment and conditioning of said keratinous tissues and said adjacent tissues, according to claim 1, wherein:

a. said alkylated nonionic surfactant having anti-static properties.

5. A composition for treatment and conditioning os said keratinous tissues and said adjacent tissues, according to claim 1, further consisting essentially of:

a. a moisturizing agent present in a range of about 0.1 to 2.0 percent by weight.

6. A composition for the treatment and conditioning of said keratinous tissues and said adjacent tissues, according to claim 5, further consisting essentially of:

a. a buffering agent present in a range of about 0.1 to 3.0 percent by weight in an amount sufficient to adjust the pH between 6.5 and 7.5, and b. said buffering agent contributes to chelation and translocation of minerals for peptide bonding.

7. A composition for the treatment and conditioning of said keratinous tissues and said adjacent tissues, according to claim 6, wherein:

a. said water present in the range of about 75 to 99 percent by weight, and b. said antimicrobial is present in the range of about 0.0 to 8.0 percent by weight, and c. said chelating agent is present in a range of about 0.5 to 10.0 percent by weight, and d. said alkylated nonionic surfactant is present in the range of about 0.0 to 3.0 percent by weight;

e. said keratinous tissues being those of finger and toe nails, and f. said adjacent tissues being cuticle, root and matrix beds, and surrounding skin of human finger and toe nails.

8. A composition for treatment and conditioning of said keratinous tissues and said adjacent tissues, according to claim 6, wherein:

a. said water is present in the range of about 75 to 99 percent by weight, and b. said antimicobial is present in the range of about 0.0 to 8.0 percent by weight, and c. said chelating agent is present in the range of about 0.1 to 10.0 percent by weight, and d. said alkylated nonionic surfactant is present in the range of about 0.0 to 3.0 percent by weight;

e. said keratinous tissues being those of equine hooves, and f. said adjacent tissues being coronet band, sole, frog, and heel bulbs of equine hooves.

9. A composition for treatment and conditioning of keratinous, hairless, tissues and their adjacent tissues such as those of equine hooves and human finger and toe nails that have been damaged by environmental factors, consisting essentially of:

a. 80 to 99 percent by weight of water, and b. 0.0 to 5.0 percent by weight of an antimicrobial, and c. 0.5 to 5.0 percent by weight of a chelating agent, and d. 0.0 to 2.5 percent by weight of an alkylated nonionic surfactant;

e. said composition being effective for curing bacterial and fungal infections of said keratinous tissues and said adjacent tissues with good residual properties.

10. A composition according to claim 9, further consisting essentially of:

a. a moisturizing agent present within a range of about 0.1 to 1.0 percent by weight;

b. said moisturizing agent being selected from a class of hygroscopic sugar alcohols for the purpose of maintaining a softness to cuticles and coronet bands of horses.

11. A composition according to claim 10, further consisting essentially of:

a. a buffering agent present within a range of about 0.1 to 2.0 percent by weight in an amount sufficient to adjust the pH between 6.5 and 7.5, and b. said buffering agent also being a chelating agent.

12. A composition, according to claim 11, for treatment and conditioning of human finger and toe nails and their said adjacent tissues, further consisting essentially of:

a. said water is present in a range of about 90 to 99 percent by weight, and b. said antimicrobial, being an alkylated quaternary ammonium compound, present in a range of about 0.0 to 2.5 percent by weight, and c. said chelating agent, being a salt of EDTA, present in a range of about 0.5 to 2.5 percent by weight, and d. said alkylated nonionic surfactant, being selected from a group of alkylated phenoxypolyoxyethelene ethanols, present in a range of about 0.0 to 2.0 percent by weight, and e. said moisturizing agent being selected from a class of hygroscopic sugar alcohols, present in a range of about 0.1 to 1.0 percent by weight, and f. said buffering agent, also being a chelating agent such as citric acid, is present in a range of about 0.1 to 2.0 percent by weight in an amount sufficient to adjust the pH between 6.5 and 7.5;

g. whereby said composition impart a strength and hardness to nails, softness to cuticle, and normal, healthy compositional balance to said adjacent tissues.

13. A composition, according to claim 12, for treatment and conditioning of said equine hooves and said adjacent tissues, further consisting essentially of:
   a. said water present in a range of about 90 to 99 percent by weight, and
   b. said antimicrobial present in a range of about 0.0 to 2.5 percent by weight, and
   c. said chelating agent present in a range of about 0.5 to 2.5 percent by weight, and
   d. said alkylated nonionic surfactant present in a range of about 0.0 to 2.0 percent by weight, and
   e. said moisturizing agent present in a range of about 0.1 to 1.0 percent by weight, and
   f. said buffering agent present in a range of about 0.1 to 2.0 percent by weight;
   g. whereby said composition imparts strength and hardness to equine hooves, maintains a softness to coronet bands, and establishes normal, healthy compositional balance and flexible functionality to said adjacent tissues.

14. A method for treatment and conditioning of keratinous, hairless, tissues and their adjacent tissues such as those of equine hooves and human finger and toe nails that have been damaged by environmental factors, which comprises the steps of:
   a. applying a safe, aqueous composition consisting essentially of:
      1). 65 to 99 percent by weight of water, and
      2). 0.0 to 10.0 percent by weight of an antimicrobial, and
      3). 0.1 to 15 percent by weight of a chelating agent, and
      4). 0.0 to 5.0 percent by weight of an alkylated nonionic surfactant;
   b. applying said composition to a plurality of keratinous, hairless, tissues and a plurality of their adjacent tissues disinfects said tissues, restores and establishes normal, healthy function and compositional balance;
   c. applying said composition to said tissue is rapidly absorbed in one to three minutes and imparts strength, hardness and flexibility with good residual activity that heals cracking and splitting of such tissues;
   d. applying said composition to said tissues on a daily basis for approximately one to two weeks followed by occasional treatments, as needed, to maintain normalcy,
   e. applying said composition to said tissues is effective for conditions that are either too wet or too dry.

15. A method for treatment and conditioning of said keratinous tissues and said adjacent tissues by application of a composition according to claim 14, wherein:
   a. said composition includes:
      1). 0.1 to 2.0 percent by weight of a moisturizing agent;
   b. said moisturizing agent being necessary to impart softness to certain said adjacent tissues.

16. A method for treatment and conditioning of said keratinous tissues and said adjacent tissues by application of a composition according to claim 15, wherein:
   a. said composition includes:
      1). 0.1 to 3.0 percent by weight of a buffering agent in an amount sufficient to adjust the pH between 6.5 and 7.5, a physiological range.
      2). said buffering agent having the property of being a chelating agent.

17. A method for treatment and conditioning of said keratinous tissues, and their said adjacent tissues, by application of a composition according to claim 16, wherein:
   a. said composition includes:
      1). said water present in a range of about 90 to 99 percent by weight, and
      2). said antimicrobial present in a range of about 0.0 to 2.5 percent by weight, and
      3). said chelating agent present in a range of about 0.5 to 2.5 percent by weight, and
      4). said alkylated nonionic surfactant present in a range of about 0.0 to 2.0 percent by weight, and
      5) said moisturizing agent present in a range of about 0.1 to 1.0 percent by weight, and
      6). said buffering agent present in a range of about 0.1 to 2.0 percent by weight in an amount sufficient to adjust the pH between 6.5 and 7.5;
   b. said keratinous tissues being those of finger and toes nails, and
   c. said adjacent tissues being cuticle, root and matrix beds, and surrounding skin of human finger and toe nails.

18. A method for treatment and conditioning of finger and toe nails, and their adjacent tissues, by application of said composition according to claim 17, whereby:
   a. the composition is quick, clean and easy to apply, such as by drops or spraying, and
   b. the composition is rapidly absorbed in approximately one minute, and
   c. nails and adjacent tissues are cleansed and disinfected, with good residual properties, and
   d. the composition imparts strength and hardness to nails as compositional balance and normalcy is established.

19. A method for treatment and conditioning of said keratinous tissues and their said adjacent tissues, by application of a composition according to claim 17, wherein:
   a. said keratinous tissues being those of equine hooves, and
   b. said adjacent tissues being coronet band, sole, frog, and heel bulbs of equine hooves.

20. A method for treatment and conditioning of equine hooves and their said adjacent tissues by application of said composition according to claim 17, whereby:
   a. said composition is quick, clean and easy to apply, such as by drops or spraying, and
   b. said composition is rapidly absorbed in approximately three minutes, and
   c. said composition cleans and disinfects hooves and their adjacent tissues with good residual properties, and
   d. said composition having anti-static properties that minimizes dirt cling to hooves, and
   e. said composition imparts strength, hardness and resiliency necessary for normal functioning as compositional balance is established, and
   f. said composition stops cracking, splitting and peeling of such tissues damaged by environmental factors and normal, healthy tissues are restored as compositional balance and functional normalcy is established.

* * * * *